(12) United States Patent
Putty et al.

(10) Patent No.: US 9,784,657 B2
(45) Date of Patent: Oct. 10, 2017

(54) APPARATUS AND METHODS FOR DENSITY AND MASS FLOW SENSING WITH A MICROMACHINED DUAL-TUBE RESONATOR

(71) Applicant: Integrated Sensing Systems, Inc., Ypsilanti, MI (US)

(72) Inventors: Michael William Putty, Grosse Pointe Woods, MI (US); Richard Thayre Smith, Saline, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 0 days.

(21) Appl. No.: 14/525,508

(22) Filed: Oct. 28, 2014

(65) Prior Publication Data

US 2015/0114137 A1  Apr. 30, 2015

Related U.S. Application Data

(60) Provisional application No. 61/961,965, filed on Oct. 28, 2013.

(51) Int. Cl.
*G01N 9/00* (2006.01)
*G01N 11/04* (2006.01)
(Continued)

(52) U.S. Cl.
CPC .......... *G01N 11/04* (2013.01); *G01F 1/8445* (2013.01); *G01F 1/8472* (2013.01); *G01N 9/002* (2013.01); *G01N 9/32* (2013.01); *G01N 2009/006* (2013.01)

(58) Field of Classification Search
None
See application file for complete search history.

(56) References Cited

U.S. PATENT DOCUMENTS 5,027,662 A   7/1991  Titlow et al.
5,663,509 A *  9/1997  Lew ...................... G01F 1/8413
                                              73/861.355
(Continued)

FOREIGN PATENT DOCUMENTS

JP   406007408   *  1/1994
WO  2009102796 A1   8/2009

OTHER PUBLICATIONS

Tom O'Banion, "Coriolis: The Direct Approach to Mass Flow Measurement," CEP, Mar. 2013, pp. 41-46, Internet: <http: www.aiche.org/cep>, American Institute of Chemical Engineers (AIChE).
(Continued)

*Primary Examiner* — Robert R Raevis
(74) *Attorney, Agent, or Firm* — Cooley LLP

(57) ABSTRACT

In some embodiments, an apparatus includes a base structure and a tube. The tube has a first tube portion, a second tube portion substantially parallel to the first tube portion, an inlet portion, and an outlet portion. The tube is configured to have a material pass from the inlet portion to the outlet portion. The apparatus further includes a drive element in contact with the tube. The drive element is configured to vibrate the tube such that the first tube portion conducts vibrational movements out of phase with vibrational movements of the second tube portion. The apparatus also includes a sensing element, at least a portion of which is in contact with the tube. The sensing element is configured to sense deflections of the first tube portion and the second tube portion such that at least one property of the material is determined.

15 Claims, 12 Drawing Sheets

(51) Int. Cl.
*G01N 9/32* (2006.01)
*G01F 1/84* (2006.01)

(56) References Cited

U.S. PATENT DOCUMENTS

| | | | |
|---|---|---|---|
| 6,477,901 | B1 | 11/2002 | Tadigadapa et al. |
| 6,883,387 | B2 * | 4/2005 | Bitto .................... G01F 1/8413 73/861.355 |
| 7,263,882 | B2 | 9/2007 | Sparks et al. |
| 7,923,194 | B2 | 4/2011 | Kohl et al. |
| 8,272,274 | B2 | 9/2012 | Sparks et al. |
| 8,365,614 | B2 | 2/2013 | Shimizu et al. |
| 8,695,418 | B2 | 4/2014 | Sparks et al. |
| 2008/0314161 | A1 | 12/2008 | Sparks et al. |
| 2010/0037706 | A1 * | 2/2010 | Sparks ................... G01F 1/8409 73/861.355 |
| 2010/0037708 | A1 | 2/2010 | Sparks et al. |
| 2010/0253169 | A1 * | 10/2010 | El-Refaie ............. H02K 1/2766 310/156.01 |
| 2011/0000315 | A1 * | 1/2011 | Tsubota ................ G01F 1/8418 73/861.357 |
| 2012/0042732 | A1 * | 2/2012 | Zhu .......................... G01F 1/74 73/861.18 |

OTHER PUBLICATIONS

D. Sparks et al., "Chip-Level Vacuum Packaging of Micromachines Using NanoGetters," IEEE Transactions on Advanced Packaging, vol. 26, No. 3, Aug. 2003, (10 pgs.).

D. Sparks et al., "A Portable MEMS Coriolis Mass Flow Sensor," IEEE Sensors Conference 2003, Toronto, Canada, No. 8.4, p. 90, Oct. 2003, (3 pgs.).

D. Sparks et al., "Coriolis Mass Flow, Density and Temperature Sensing With a Single Vaccum Sealed MEMS Chip," Solid-State Sensor, Actuator and Microsystems Workshop, Hilton Head Island, South Carolina, Jun. 6-10, 2004, (4 pgs.).

Richard Smith et al., "A MEMS-based Coriolis Mass Flow Sensor for Industrial Applications," IEEE Transactions on Industrial Electronics, vol. 56, No. 4, Apr. 2009, (7 pgs.).

W.D. Beaver, "All Quartz Surface Mount Resonators," 2001 IEEE International Frequency Control Symposium and PDA Exhibition, (7 pgs.).

International Search Report/Written Opinion mailed Jan. 22, 2015 for PCT Application PCT/US2014/062681.

Haneveld et al., "Micro Coriolis Mass Flow Sensor with Integrated Capacitive Readout", Micro Electro Mechanical Systems (MEMS), IEEE 22nd International Conference, Jan. 25-29, 2009, pp. 463-466.

Nasiri, Steven, "A Critical Review of MEMS Gyroscopes Technology and Commercialization Status", InvenSense Inc., San Jose, CA, Dec. 6, 2010, 8 pgs., http://www.invensense.com/mems/gyro/documents/whitepapers/MEMSGyroComp.pdf.

Corman et al., "A Low-Pressure Encapsulated Resonant Fluid Density Sensor with Feedback Control Electronics", Measurement Science and Technology, IOP, Bristol, GB, vol. 11, No. 3, Mar. 1, 2000, 7 pgs.

Extended European Search Report issued to European patent application No. 14857410.6, Feb. 15, 2017, 8 pgs.

* cited by examiner

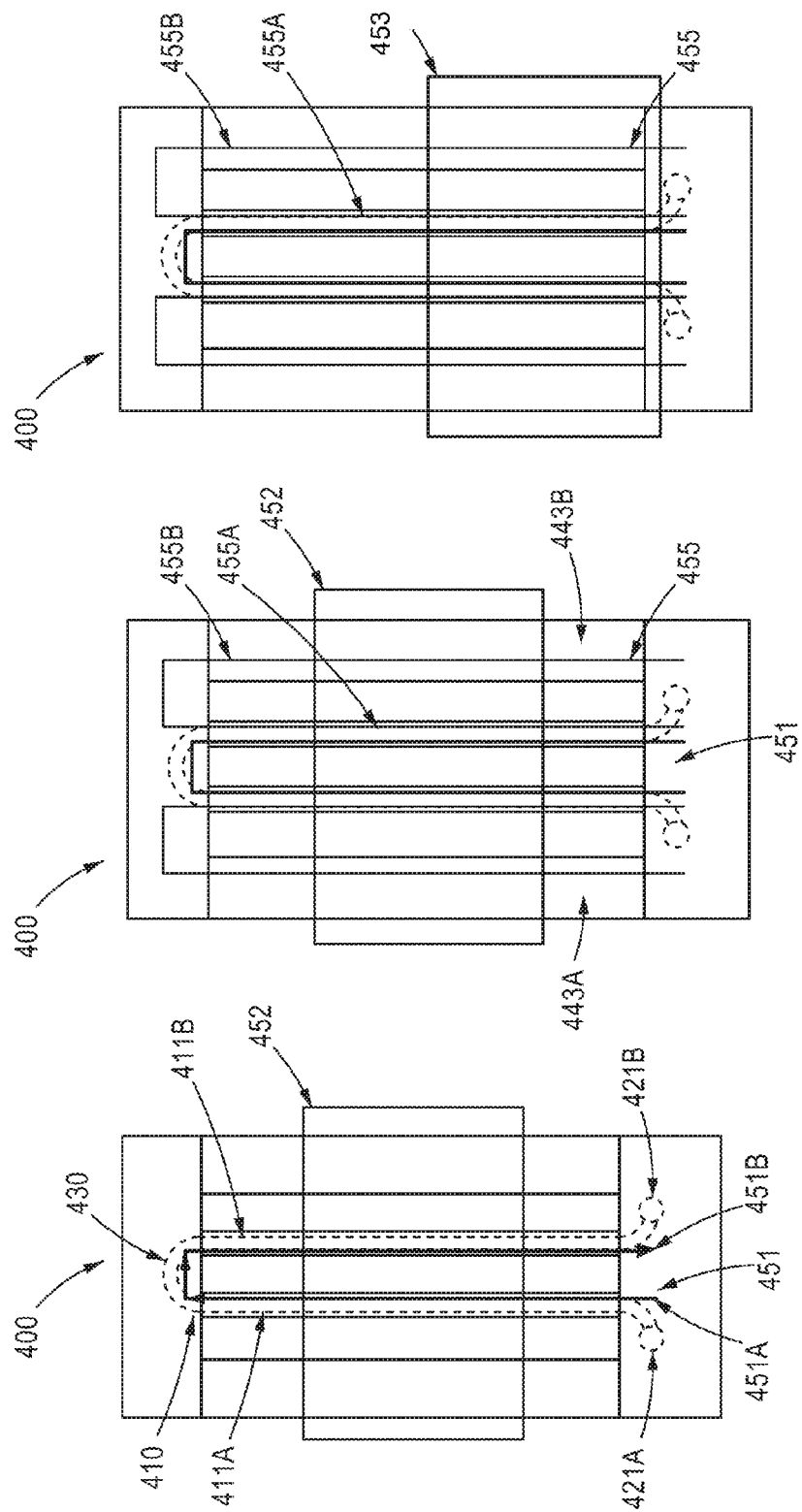

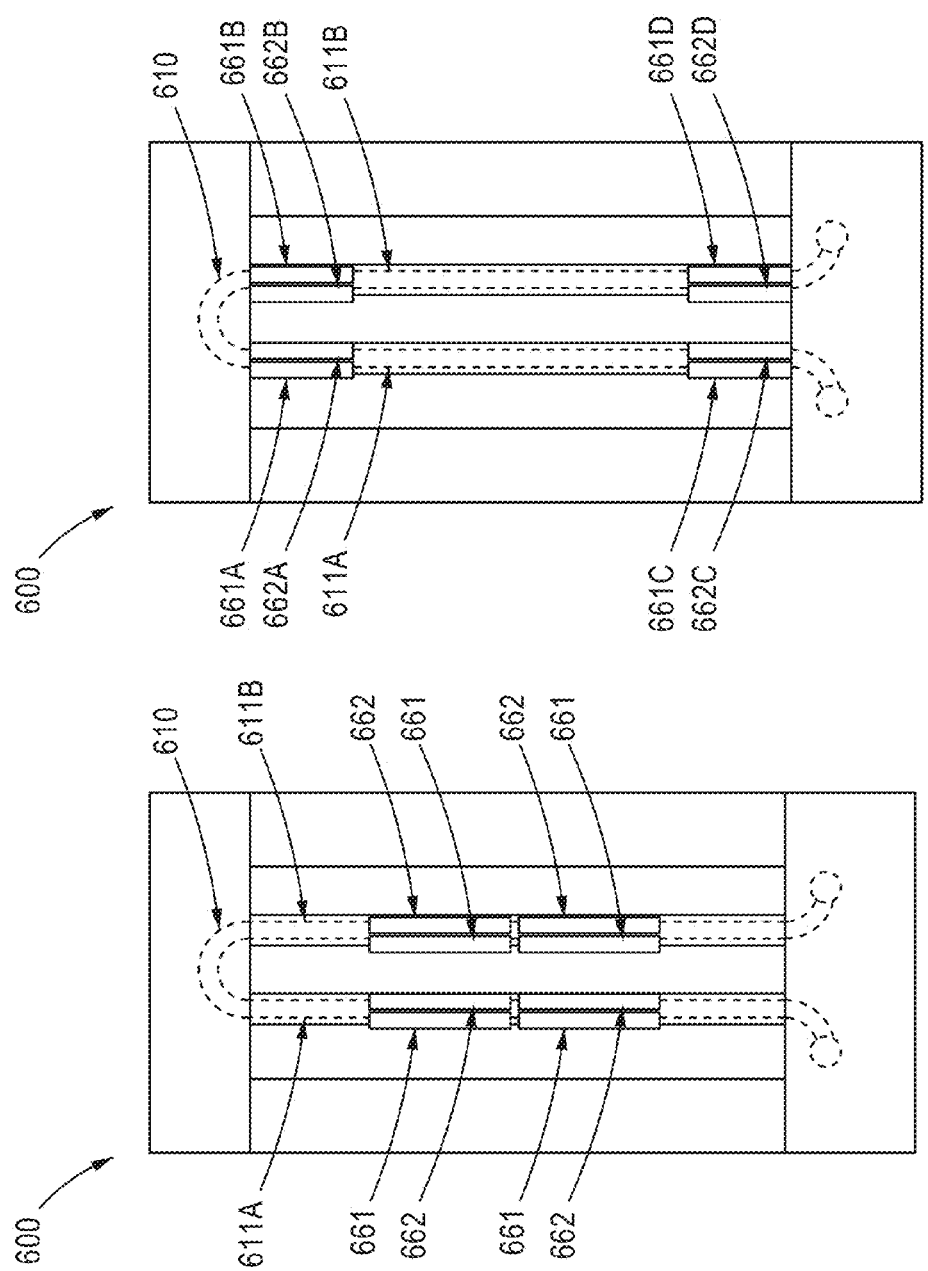

1100

```
┌─────────────────────────────────────────────┐
│ Pass a material from an inlet portion of a  │
│ tube to an outlet portion of the tube       │
│ through an internal cavity passage. The     │
│ tube has a first tube portion and a         │
│ second tube portion substantially parallel  │
│ to the first tube portion. The first tube   │
│ portion is coupled to the inlet portion and │
│ the second tube portion is coupled to the   │
│ outlet portion. The internal cavity passage │
│ is defined at least in part by the first    │
│ tube portion and the second tube portion.   │
│                   1102                      │
└─────────────────────────────────────────────┘
                      │
                      ▼
┌─────────────────────────────────────────────┐
│ Operate a drive element in contact with the │
│ tube to induce vibrational movements of the │
│ first tube portion and the second tube      │
│ portion.                                    │
│                   1104                      │
└─────────────────────────────────────────────┘
                      │
                      ▼
┌─────────────────────────────────────────────┐
│ Sense deflections of the first tube portion │
│ and the second tube portion.                │
│                   1106                      │
└─────────────────────────────────────────────┘
                      │
                      ▼
┌─────────────────────────────────────────────┐
│ Determine at least one property of the      │
│ material based on the sensed deflections.   │
│                   1108                      │
└─────────────────────────────────────────────┘
```

FIG.11

APPARATUS AND METHODS FOR DENSITY AND MASS FLOW SENSING WITH A MICROMACHINED DUAL-TUBE RESONATOR

CROSS REFERENCE TO RELATED APPLICATION

This application claims priority to and benefit of U.S. Provisional Patent Application No. 61/961,965, filed Oct. 28, 2013, and entitled "Balanced Dual-tube MEMS Resonator Design for Density and Mass Flow Sensing", the disclosure of which is incorporated herein by reference in its entirety.

BACKGROUND

Some embodiments described herein relate generally to apparatus and methods for microelectromechanical systems (MEMS) for density and mass flow sensing. More particularly, but not by way of limitation, some of the embodiments described herein relate to apparatus and methods for density and mass flow sensing using a balanced dual-tube MEMS resonator.

Mass flow and fluid density sensors using MEMS technology have been used in a variety of industries, including, for example, medical treatment systems such as drug infusion (delivery) and anesthetic delivery equipment, energy and fuel systems including fuel delivery systems and fuel cell systems such as direct methanol fuel cells (DMFC), chemical processing systems, and consumer goods. Coriolis-based microfluidic devices have provided accurate measurements of mass flow and fluid density. Some known Coriolis-based microfluidic devices include a micromachined tube supported above a substrate to have a free-standing portion. A drive mechanism is used to drive the free standing portion of the tube at or near resonance, while a sensing mechanism senses the Coriolis deflections of the resonating tube. The fluid density and the mass flow rate can therefore be deduced from the resonance frequency and the Coriolis deflections. The performance of these devices, however, is reduced due to mechanical losses resulting from attachment of the resonating tube to the substrate. Additionally, a relatively large packaging mass is used to dissipate the mechanical energy loss and isolate the resonating tube from external mechanical stress and vibration.

Accordingly, a need exists for apparatus and methods for a dual-tube MEMS design for density and mass flow sensing with efficient and controllable detection mechanisms.

SUMMARY

In some embodiments, an apparatus includes a base structure and a tube. The tube has a first tube portion, a second tube portion substantially parallel to the first tube portion, an inlet portion, and an outlet portion. The first tube portion is coupled to the inlet portion and the second tube portion is coupled to the outlet portion. The inlet portion and the outlet portion are further connected to the base structure. The tube is also configured to have a material pass from the inlet portion to the outlet portion through a cavity defined at least in part by the first tube portion and the second tube portion. The apparatus further includes a drive element in contact with the tube. The drive element is configured to vibrate the tube such that the first tube portion conducts vibrational movements out of phase with vibrational movements of the second tube portion. The apparatus also includes a sensing element. At least a portion of the sensing element is in contact with the tube. The sensing element is also configured to sense deflections of the first tube portion and the second tube portion such that at least one property of the material is determined when the material passes through the tube and the tube is vibrated by the drive element.

BRIEF DESCRIPTION OF THE DRAWINGS

FIGS. 4A-4C are top views of a magnetically actuated and sensed dual-tube MEMS device, according to an embodiment.

FIGS. 6A-6B are top views of a dual-tube MEMS device actuated and sensed by piezoelectric electrodes, according to an embodiment.

FIG. 11 is a flow chart describing a method of operating the dual-tube MEMS device, according to an embodiment.

DETAILED DESCRIPTION

Figure 1A:
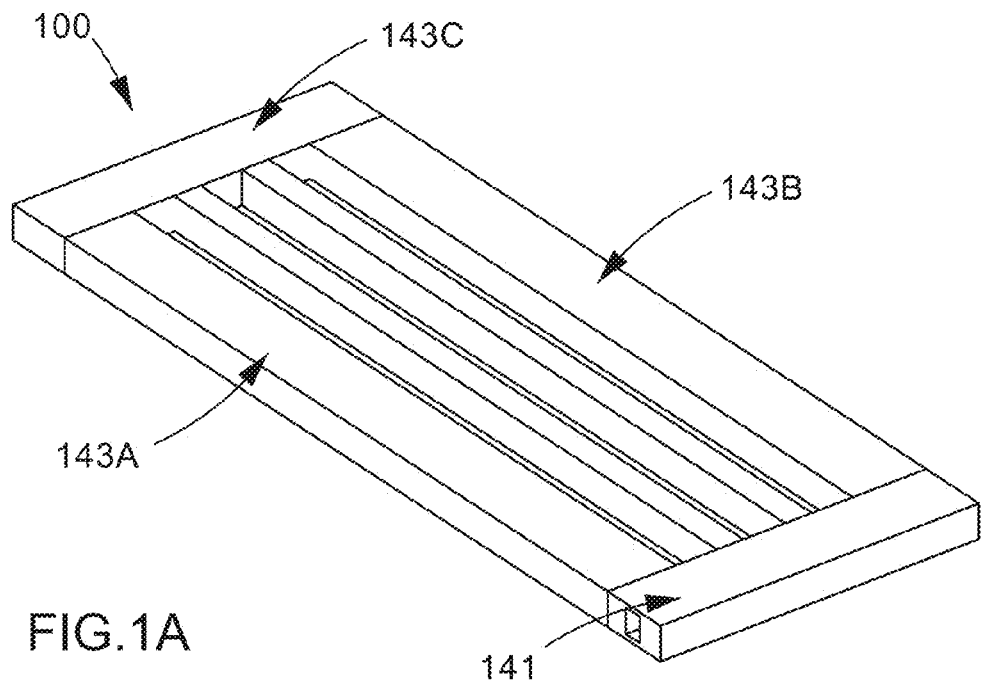
FIGS. 1A-1B are schematic illustrations of a dual-tube MEMS device, according to an embodiment.

Apparatus and methods for density and mass flow sensing with a micromachined dual-tube resonator are described herein. In some embodiments, an apparatus includes a base structure and a tube. The tube has a first tube portion, a second tube portion substantially parallel to the first tube portion, an inlet portion, and an outlet portion. The first tube portion is coupled to the inlet portion and the second tube portion is coupled to the outlet portion. The inlet portion and the outlet portion are further connected to the base structure. The tube is also configured to have a material pass from the inlet portion to the outlet portion through a cavity defined at least in part by the first tube portion and the second tube portion. The apparatus further includes a drive element in contact with the tube. The drive element is configured to vibrate the tube such that the first tube portion conducts vibrational movements out of phase with vibrational movements of the second tube portion. The apparatus also includes a sensing element. At least a portion of the sensing element is in contact with the tube. The sensing element is also configured to sense deflections of the first tube portion and the second tube portion such that at least one property of the material is determined when the material passes through the tube and the tube is vibrated by the drive element.

In some embodiments, an apparatus includes a base structure and a micromachined tube. The micromachined tube has a first tube portion, a second tube portion substantially parallel to the first tube portion, an inlet portion, and an outlet portion. The first tube portion is coupled to the inlet portion and the second tube portion is coupled to the outlet portion. The micromachined tube is further connected to the base structure via a first end portion of the micromachined tube. A second end portion of the micromachined tube is free-standing and spaced apart from the base structure. The apparatus further includes a drive element disposed in contact with the micromachined tube. The drive element is also configured to vibrate the micromachined tube when a material passes from the inlet portion to the outlet portion through a cavity defined at least in part by the first tube portion and the second tube portion. The apparatus also includes a sensing element. At least a portion of the sensing element is in contact with the micromachined tube. The sensing element is also configured to sense deflections of the first tube portion and the second tube portion such that at least one property of the material is determined when the material passes through the micromachined tube and the micromachined tube is vibrated by the drive element.

In some embodiments, a method includes passing a material from an inlet portion of a tube to an outlet portion of the tube through an internal cavity passage. The tube has a first tube portion and a second tube portion substantially parallel to the first tube portion. The first tube portion is coupled to the inlet portion and the second tube portion is coupled to the outlet portion. The internal cavity passage is defined at least in part by the first tube portion and the second tube portion. The method further includes operating a drive element in contact with the tube to induce vibrational movements of the first tube portion and the second tube portion. In some embodiments, the method includes sensing deflections of the first tube portion and the second tube portion, and determining at least one property of the material based on the sensed deflections.

As used in this specification, the singular forms "a," "an" and "the" include plural referents unless the context clearly dictates otherwise. Thus, for example, the term "a substrate" is intended to mean a single substrate or multiple substrates. For another example, the term "a metal conductor" can mean a single metal conductor or multiple metal conductors.

As used herein, the terms "about" and "approximately" generally mean plus or minus 10% of the value stated. For example, about 0.5 would include 0.45 and 0.55, about 10 would include 9 to 11, about 1000 would include 900 to 1100.

Figure 1B:
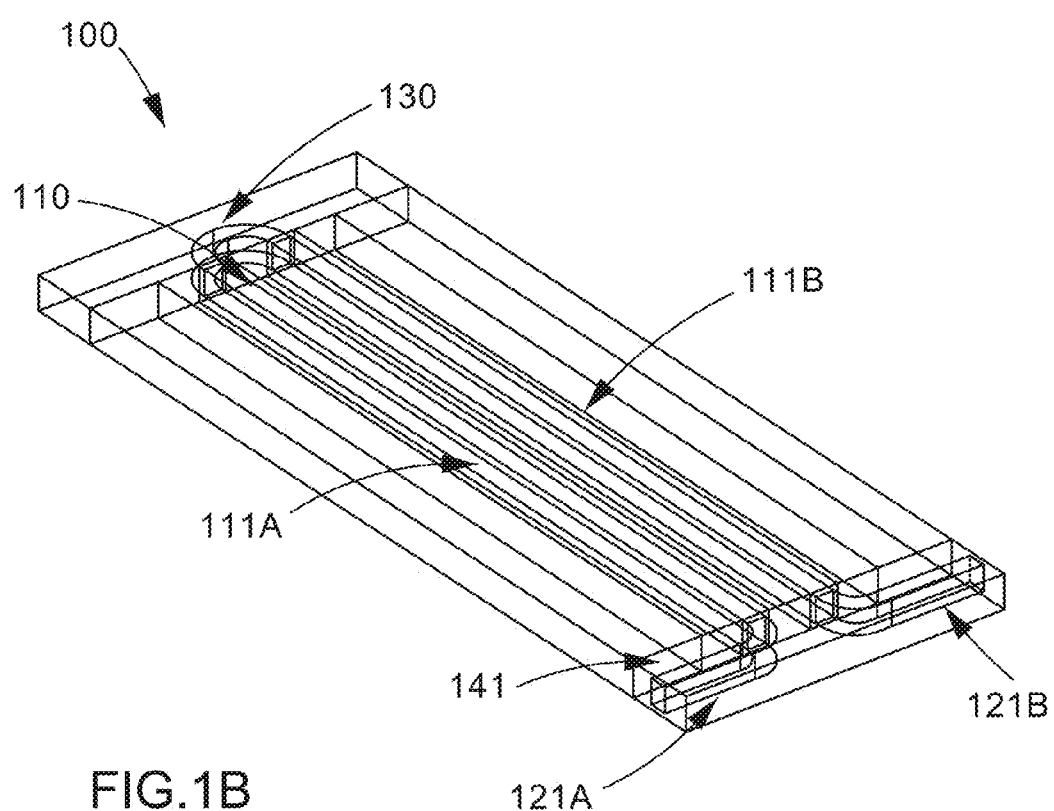

FIGS. 1A-1B are schematic illustrations of a dual-tube MEMS device, according to an embodiment. The dual-tube MEMS device 100 can be any suitable device for measuring material properties. The materials that can be used with the dual-tube MEMS device 100 include, for example, a liquid, a gas, a slurry, a suspension containing a solid or liquid dispersed phase, and/or the like. The properties which the dual-tube MEMS device 100 can measure can include, for example, mass flow rate, density, specific gravity, volumetric flow rate, dose, total volume delivered, temperature, chemical concentration, viscosity, lubricity of fluid, and/or the like. In some embodiments, the dual-tube MEMS device 100 can be used as a microfluidic device for measuring properties of fluids.

As shown in FIGS. 1A-1B, the dual-tube MEMS device 100 includes a micromachined tube 110, a base structure 141, a frame structure including portions 143A, 143B and 143C, and a substrate (not shown in FIGS. 1A-1B). The base structure 141 is fabricated on top of the substrate (not shown in FIGS. 1A-1B). The micromachined tube 110 and the portions of the frame structure 143A and 143B are coupled to the base structure 141.

The micromachined tube 110 can be formed of a material including, for example, silicon, doped silicon, other semiconductor materials, diamond, titanium and other metallic materials, dielectric materials, glass, plastic, ceramic materials, and/or other materials capable of being micromachined. The substrate (not shown in FIGS. 1A-1B) can be formed of a material including, for example, plastic, metal, glass, ceramic materials, and/or the like. The dual-tube MEMS device 100 can be fabricated using semiconductor technology. The structural components of the device can be combined with electronics on a single chip by micromachining techniques, such as bulk etching and surface thin-film etching, to yield a MEMS device capable of precisely analyzing very small quantities of material. The dual-tube MEMS device 100 described herein can be packaged in vacuum or in atmospheric pressure. Further details of the fabrication of the micromachined tube 110, the base structure 141, and the substrate are illustrated in a patent application Ser. No. 13/093,321, entitled "Fluidic Systems and Methods of Determining Properties of Fluids Flowing Therein", filed on Apr. 25, 2011, now U.S. Pat. No. 8,695, 418, which is incorporated herein by reference in its entirety.

The micromachined tube 110 includes a first tube portion 111A, a second tube portion 111B, an inlet portion 121A, an outlet portion 121B, and a curved portion 130. The first tube portion 111A and the second tube portion 111B are substantially parallel with each other when the first tube portion 111A and the second tube portion 111B are not in vibration mode. The first tube portion 111A and the second tube portion 111B are connected together via the curved portion 130 disposed within the frame portion 143C. The first tube portion is coupled to the inlet portion 121A, and the second tube portion is coupled to the outlet portion 121B. The first tube portion 111A, the second tube portion 111B, the inlet portion 121A, the outlet portion 121B, and the curved portion 130 together define a continuous internal cavity and/or canal for a material to pass through.

In use, the material can enter the cavity of the micromachined tube 110 at the inlet portion 121A, and leave the micromachined tube 110 at the outlet portion 121B (or vice versa). Specifically, an end portion of the inlet portion 121A defines an aperture through which the material can enter and/or exit the micromachined tube 110. Similarly, an end portion of the outlet portion 121B defines an aperture through which the material can enter and/or exit the micromachined tube 110.

Figure 2A:
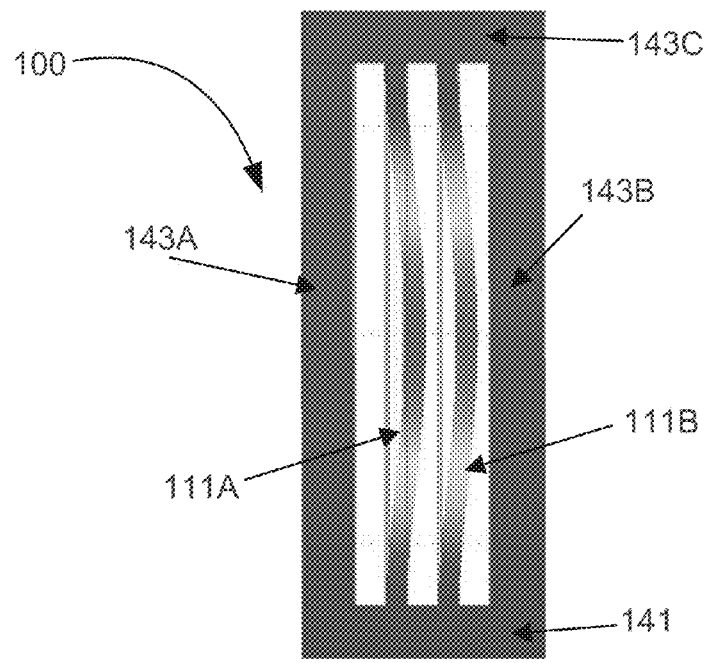
FIGS. 2A-2B are optical illustrations of a dual-tube MEMS device vibrating in phase and out of phase, respectively, according to an embodiment.
Figure 2B:
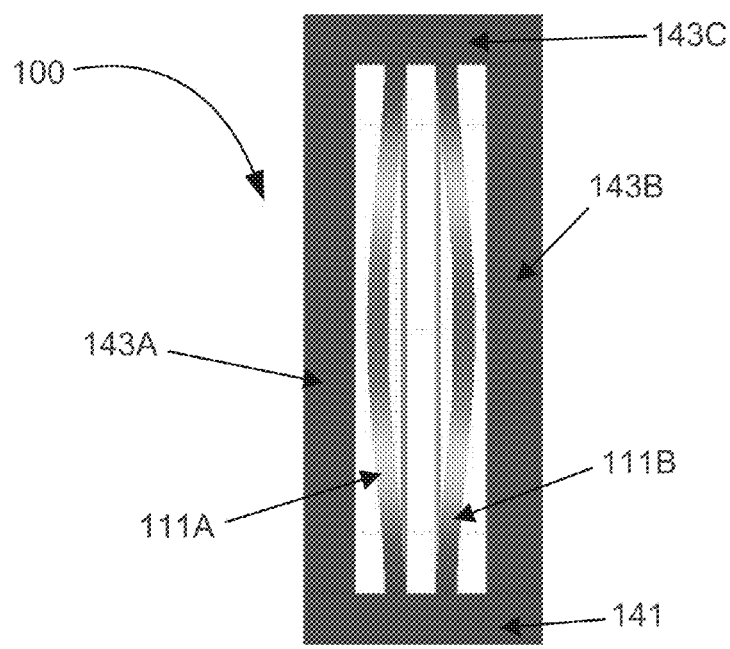

The micromachined tube 110 is coupled to the base structure 141 through the inlet portion 121A and the outlet portion 121B. The first tube portion 111A, the curved portion 130, and the second tube portion 111B are situated above a surface of the substrate (not shown in FIGS. 1A-1B). The first tube portion 111A, the curved portion 130, and the second tube portion 111B lie in a plane that is substantially parallel to the substrate surface and a gap is defined between the micromachined tube 110 and the substrate. The first tube portion 111A and the second tube portion 111B are also coupled to the frame portion 143C, which includes the curved portion 130. Thus, the end points of the first tube portion 111A are fixed to the inlet portion and the frame portion 143C. Similarly, the end points of the second tube portion 111B are fixed to the outlet portion 121B and the frame portion 143C. Accordingly, a middle portion of the first tube portion 111A and the second tube portion 111B can vibrate as shown in FIGS. 2A and 2B (described in further detail herein).

Additionally, the frame portion 143C can be free-standing. Similarly stated, the frame portion 143C is not directly coupled to the base structure 141. Instead the frame portion 143C is coupled to the base structure via the frame portions 143A and 143B. Thus, the tube portions 111A and 111B and the frame portions 143A, 143B and 143C act as a free-standing cantilever with one end coupled to the base 141 and the other end free-standing (i.e., not coupled to the base). This allows the frame portions 143A, 143B and 143C as well as the tube portions 111A and 111B to move in a direction perpendicular to a plane defined by the micromachined tube 110 when actuated. In some implementations, the micromachined tube 110 is a balanced sensor and does not need to be fixed to the base structure 141 or the frame portion 143C. In this implementation, the micromachined tube 100 can vibrate in free space. There are no unbalanced forces or torques from the vibrating element. Therefore, the micromachined tube 100 can be decoupled from the base structure 141 or the frame portion 143C.

In some embodiments, a material enters and exits the micromachined tube 110 via the apertures defined by the inlet portion 121A and the outlet portion 121B, respectively. The first tube portion 111A and the second tube portion 111B are configured to vibrate at or near the resonant frequency to determine properties of the material passing through the micromachined tube 110 using Coriolis force principles. The vibrational movements of the first tube portion 111A and the second tube portion 111B are in a direction parallel to the plane in which they lie and parallel to the substrate surface (not shown in FIGS. 1A-1B). The first tube portion 111A and the second tube portion 111B can be configured to vibrate in phase with each other, as shown in FIG. 2A, or about 180 degrees out of phase with each other, as shown in FIG. 2B. In one implementation, the vibration mode in which the first tube portion 111A and the second tube portion 111B vibrate about 180 degrees out of phase with each other can be used for density and mass flow measurements.

In some embodiments, as the first tube portion 111A and the second tube portion 111B are driven and vibrate out of phase at or near resonance, a twisting motion of the first tube portion 111A and the second tube portion 111B, referred to as the Coriolis effect, can be measured. The degree to which the first tube portion 111A and the second tube portion 111B twists (or deflects) during a vibration cycle as a result of the Coriolis effect can be correlated to the mass flow rate of the material passing through the micromachined tube 110, while the density of the material is proportional to the frequency of vibration at resonance.

Figure 3A:
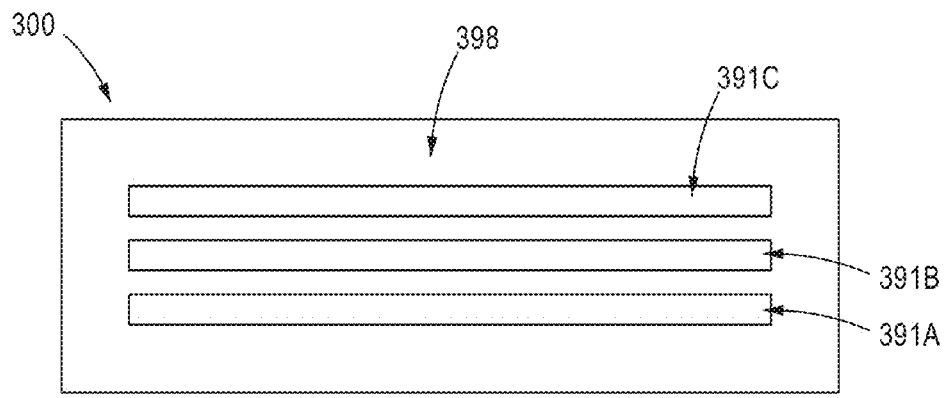
FIG. 3A is a top view of a dual-tube MEMS device with gap structures, according to an embodiment.

FIG. 3A is a top view of a dual-tube MEMS device with gap structures, according to an embodiment. The dual-tube MEMS device 300 is structurally and/or functionally similar to the dual-tube MEMS device 100 described in FIGS. 1A-1B. As described above, in some embodiments, the vibrational movements of the dual-tube MEMS device 300 are substantially in a direction parallel to the plane in which it lies and substantially parallel to the substrate surface (not shown in FIG. 3A). In some embodiments, the micromachined tube (not shown in FIGS. 3A-3B) included in the dual-tube MEMS device 300 can also be induced with up and down movements relative to the plane of the micromachined tube, similar to movements of a cantilever, while the micromachined tube vibrates in the direction parallel to the plane in which it lies. Similarly stated, the micromachined tube can move substantially perpendicular to the substrate as well as substantially parallel to the substrate. In some embodiments, in order to damp the cantilever motion (i.e., up and down movements relative to the plane of the micromachined tube) without significantly limiting the side-to-side vibration movements, squeeze film damping can be implemented.

In some implementations, air gaps, such as gaps 391A, 391B, 391C shown in FIG. 3A are defined in between the first tube portion, the second tube portion, and the two frame structures (similar to 111A, 111B, 143A, and 143B shown in FIGS. 1A-1B) to provide space for the micromachined tube's side-to-side vibrations. The gap 391A is defined between the first tube portion (similar to 111A in FIGS. 1A-1B) and a frame structure (similar to 143A in FIGS. 1A-1B), the gap 391B is defined between the first tube portion (similar to 111A in FIGS. 1A-1B) and the second tube portion (similar to 111B in FIGS. 1A-1B), and the gap 391C is defined between the second tube portion (similar to 111B in FIGS. 1A-1B) and a frame structure (similar to 143B in FIGS. 1A-1B). Accordingly, gaps 391A, 391B, and 391C are defined within the plane of the micromachined tube.

Figure 3B:
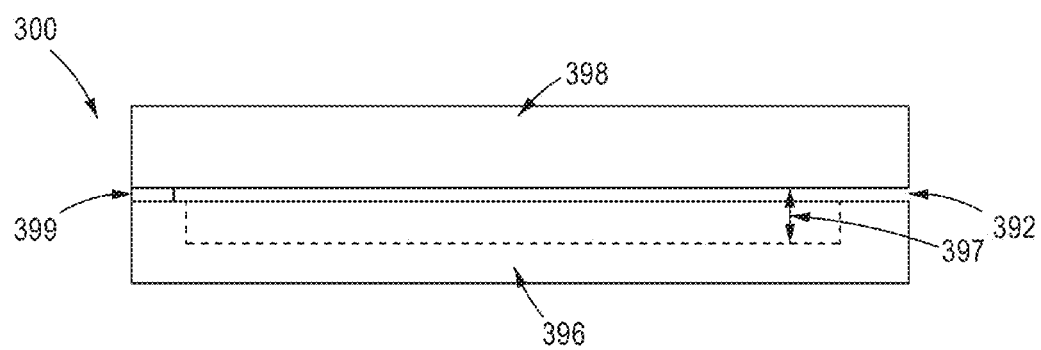
FIG. 3B is a side view of a dual-tube MEMS device with gap structures, according to an embodiment.

Air gaps, such as gaps 392 and 397 shown in FIG. 3B are defined between the frame structure 398 and the substrate underneath 396 (and disposed substantially parallel to) the frame structure 398 to damp the cantilever motion of the micromachined tube. FIG. 3B is a side view of a dual-tube MEMS device defining a large gap 397 and narrow gap 392, according to an embodiment. The large gap 397 is defined between the tube (including the first tube portion and the second tube portion) and the substrate 398. The large gap 397 allows movement of tubes with respect to the substrate 398. The narrow gap 392 is defined between the frame portion 398 and the substrate 396. The narrow gap 392 is defined smaller than the large gap 397 to dampen the movement of the frame portion 398 with respect to the substrate 396. In some implementations, the large air gap 397 can have a width of approximately 5 µm-200 µm. For example, the large air gap 397 can have a width of approximately 100 µm. In some implementations, the narrow air gap 392 can have a width of approximately 0.5 µm-50 µm. For example, the narrow air gap 392 can have a width of approximately 5 µm.

FIG. 3B also illustrates the cantilever structure described with respect to FIGS. 1A and 1B. Specifically, a first end portion of the frame 398 (which holds the tube) is coupled to a base 399 while a second end portion of the frame 398 is suspended above the substrate 396 (i.e., is free-standing). Thus, the frame 398 (holding the tube) defines a cantilever structure, which allows some movement in a direction substantially perpendicular to a plane defined by the tube.

Figure 3C:
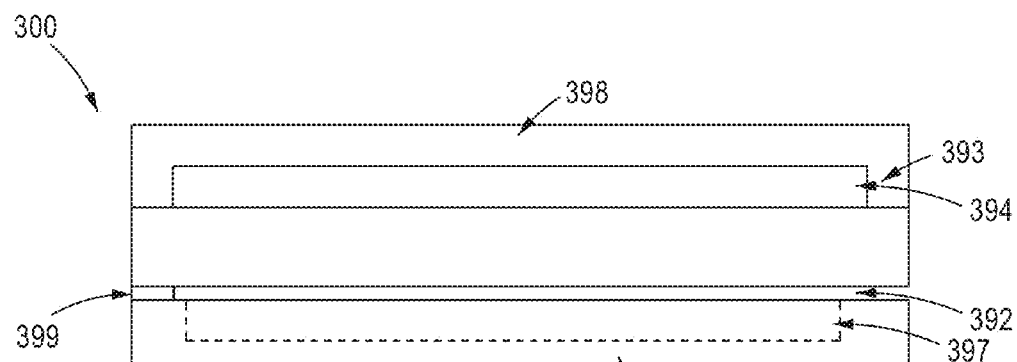
FIG. 3C is a side view of a dual-tube MEMS device with a top cap for device protection, according to an embodiment.

FIG. 3C is a side view of a dual-tube MES device with a top cap 393 for device protection, according to an embodiment. In some embodiments, a cap 393 can be disposed on top of the dual-tube MEMS device 300 to protect the device from moisture and dust. The cap 393 can define an air gap 394 to further damp the cantilever motion of the micromachined tube, in addition to the air gap 392, as described above with regards to FIG. 3B. In some implementations, the cap 393 can be attached to the dual-tube MEMS device 300 using low out-gassing resin.

FIGS. 4A-4C are top views of a magnetically actuated and sensed dual-tube MEMS device, according to an embodiment. The dual-tube MEMS device 400 includes a micromachined tube 410. The dual-tube MEMS device 400 and the micromachined tube 410 are structurally and/or functionally similar to the dual-tube MEMS device 100 and the micromachined tube 110 described in FIGS. 1A-1B. In some embodiments, the micromachined tube 410 includes a first tube portion 411A, a second tube portion 411B, an inlet portion 421A, an outlet portion 421B, and a curved portion 430. The first tube portion 411A is coupled to the inlet portion 421A, and the second tube portion 411B is coupled to the outlet portion 421B. The material can enter the micromachined tube 410 at an aperture defined by the inlet portion 421A, and leave the micromachined tube 410 at an aperture defined by the outlet portion 421B (or vice versa).

In some embodiments, actuation and/or vibration of the micromachined tube 410 is accomplished by applying a Lorentz force to each of the first tube portion 411A and the second tube portion 411B. Lorentz drive is obtained by applying a static magnetic field 452 (e.g. from a permanent magnet (not shown in FIGS. 4A-4C)) substantially perpendicular to the motion of the tubes. This causes and/or induces current to flow down the length of the micromachined tube 410 through conducting traces 451 deposited on and/or attached to the micromachined tube 410. In this actuation scheme the tuning fork mode vibration (i.e., out of phase vibration) of the micromachined tube 410 is naturally selected by having the current flow in opposite directions 451A and 451B on the first tube portion 411A and the second tube portion 411B. In some implementations, a single metal trace 451, as shown in FIG. 4A, is used. In other implementations, more than one metal trace can be used In some embodiments, sensing in the micromachined tube 410 is performed using two steps. First, a lateral tuning fork motion of the micromachined tube 410 is sensed. This signal is used in a closed loop control system so that the tuning fork mode (i.e., out of phase vibration) of the micromachined tube 410 is driven to substantially constant amplitude. Second, a Coriolis-induced bending of the first tube portion 411A and the second tube portion 411B is sensed to measure the mass flow rate in the micromachined tube 410. Both motions can be sensed by Faraday induction with the same static magnetic field 452 that is used to actuate the micromachined tube 410.

To sense the lateral tuning fork motion of the micromachined tube 410, in some implementations, as shown in FIG. 4B, a Faraday loop 455 can be formed from a conductor 455A deposited on and/or attached to the vibrating micromachined tube 410 and a conductor 455B mounted on the fixed frame structure 443B. The frame structures 443A and 443B are structurally and/or functionally similar to the frame structure 143A and 143B described in FIGS. 1A-1B. When the micromachined tube 410 is vibrating, an area defined by the Faraday loop 455 is changing and in combination with the applied static magnetic field 452 this changing Faraday loop area 455 generates a voltage proportional to the tuning fork mode amplitude by Faraday induction.

Sensing Coriolis deflections of the first tube portion 411A and the second tube portion 411B, in some implementations, uses the out-of-phase vibration of the tubes since this vibration has the same shape and is naturally driven by the Coriolis force. FIGS. 5A-5B show optical illustrations of Coriolis deflections of a tube, according to an embodiment. In a symmetric uniform magnetic field, each of the first tube portion 411A and the second tube portion 411B generates a voltage opposite to the other. Thus, the voltages cancel out each other. To solve this problem, an asymmetric magnetic field 453 can be implemented for actuation and sensing. In some implementations, the asymmetric magnetic field 453 can be concentrated in either the upper or lower half (as shown in FIG. 4C) of the micromachined tube 410. Such a magnetic field arrangement can be achieved by permanent magnet placement or a ferromagnetic magnetic circuit. This magnetic field distribution allows the Faraday loop running down the length of the tube to sense the Coriolis induced motion without using any additional structures such as silicon springs. Also, this magnetic field arrangement still allows actuation of the tuning fork mode (i.e., out of phase vibration) albeit at about half the force as the symmetric magnetic field arrangement. The reduced actuation force can be compensated with additional driving current.

Figure 4D:
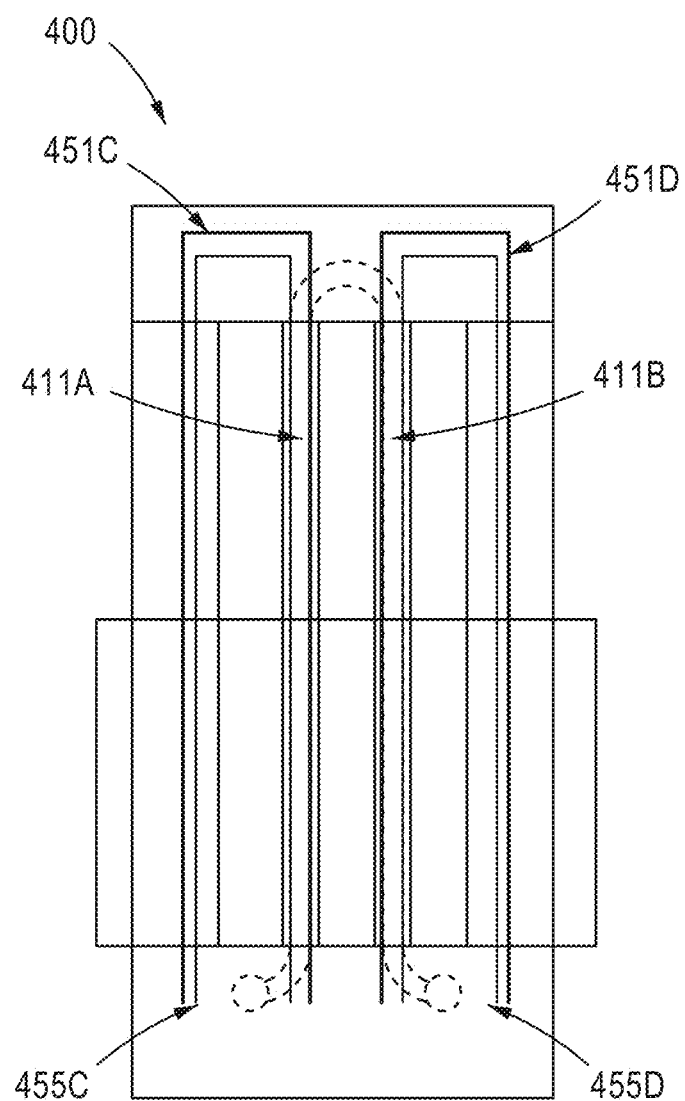
FIG. 4D shows a dual-tube MEMS device with two actuator coils, according to an embodiment.
Figure 5A:
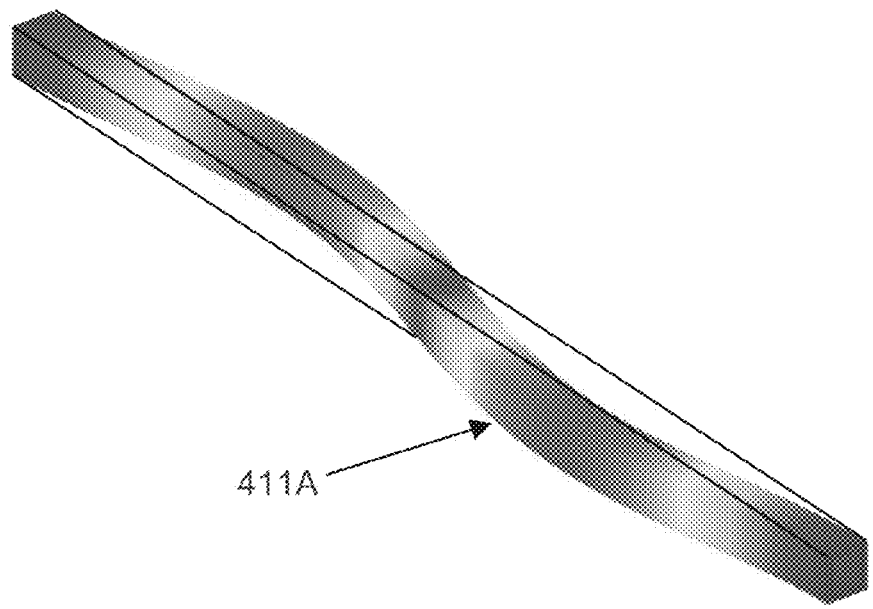
FIGS. 5A-5B show optical illustrations of Coriolis deflections of a tube, according to an embodiment.
Figure 5B:
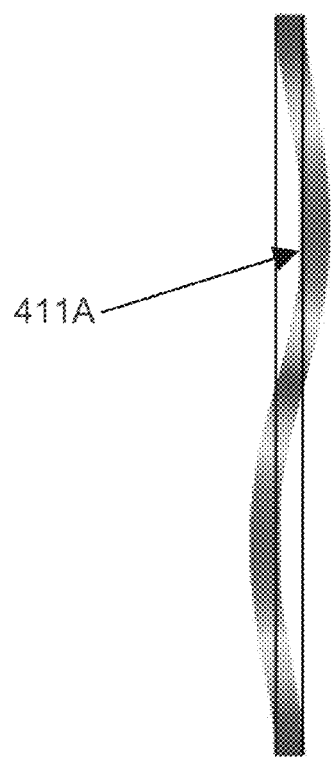

FIG. 4D shows a dual-tube MEMS device with two actuator coils, according to an embodiment. In some implementations, instead of having one coil, such as 451 in FIG. 4A, to actuate both the first tube portion 411A and the second tube portion 411B, a first coil can be used to actuate the first tube portion 411A and a second coil can be used to actuate the second tube portion 411B separately (e.g., for the purpose of minimizing zero bias draft). As shown in FIG. 4D, coil 451C can be configured to actuate the first tube portion 411A, and coil 451D can be configured to actuate the second tube portion 411B. Coils 455C and 455D can be configured to sense the Coriolis deflections of the first tube portion 411A and the second tube portion 411B, respectively, similar to 455 as previously described in FIG. 4B.

FIGS. 6A-6B are top views of a dual-tube MEMS device actuated and sensed by piezoelectric electrodes, according to an embodiment. Piezoelectric transducers (or electrodes) can be placed at areas where the structural strain in the tube to be driven or sensed is at a maximum. The force or current the piezoelectric transducers generate can be proportional to the area multiplied by the strain. These parameters and/or constrains can be used to select a size, area, and/or location for the transducers. For a dual-tube MEMS device in which the micromachined tube vibrates laterally, the transducers can be placed at the center of the first and second tube portions or at the ends of the first and second tube portions. As shown in FIGS. 6A-6B, the dual-tube MEMS device 600 includes a micromachined tube 610, which is functionally and/or structurally similar to the micromachined tube 110 described in FIGS. 1A-1B. The micromachined tube 610 includes a first tube portion 611A and a second tube portion 611B. In some implementations, two piezoelectric actuation electrodes 662 can be placed on each of the first tube portion 611A and the second tube portion 611B, and two piezoelectric sensing electrodes 661 can be placed on each of the first tube portion 611A and the second tube portion 611B. The eight piezoelectric electrodes can be placed at the center of the micromachined tube 610 covering a center point of each of the first tube portion 611A and the second tube portion 611B, as shown in FIG. 6A, according to one implementation. In another implementation, the eight piezoelectric electrodes can be placed at the end of the micromachined tube 610 covering an end point of each of the first tube portion 611A and the second tube portion 611B, as shown in FIG. 6B. In FIG. 6B, an actuator electrode 662A-662B and a sense electrode 661A-661B can be placed on the top end of each of the first tube portion 611A (662A and 661A) and the second tube portion 611B (similarly 662B and 661B), and an actuator electrode 662C-662D and a sense electrode 661C-661D can be placed on the bottom end of each of the first tube portion 611A and the second tube portion 611B, according to one embodiment. Many combinations of these locations are possible for sensor designs. For example, four actuator electrodes can be placed on each of the first tube portion 611A and the second tube portion 611B with one electrode at the top end, two electrodes in the center, and one electrode at the bottom end, and another four sensing electrodes can be placed on each of the first tube portion 611A and the second tube portion 611B with one electrode at the top end, two electrodes in the center, and one electrode at the bottom end.

Figure 8A:
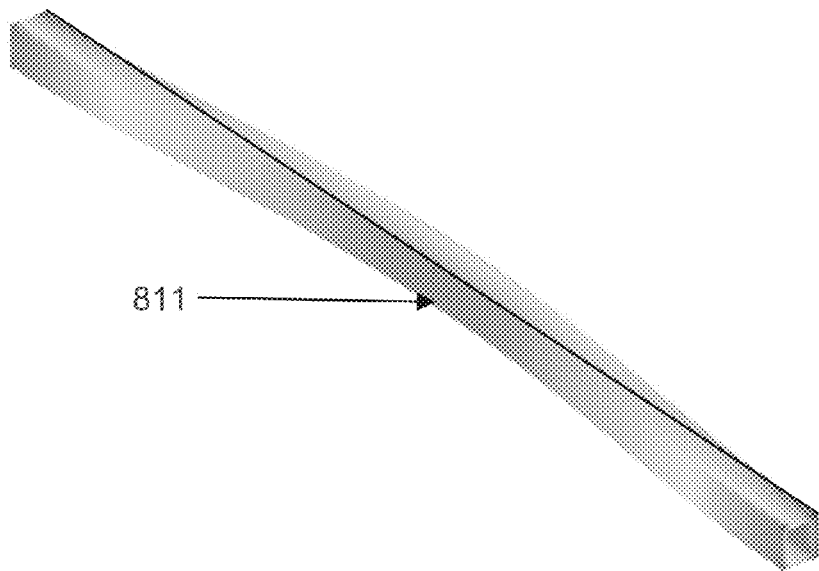
FIGS. 8A-8B show strain distribution for a single tube with vibrational movements and Coriolis deflections, according to an embodiment.
Figure 8B:
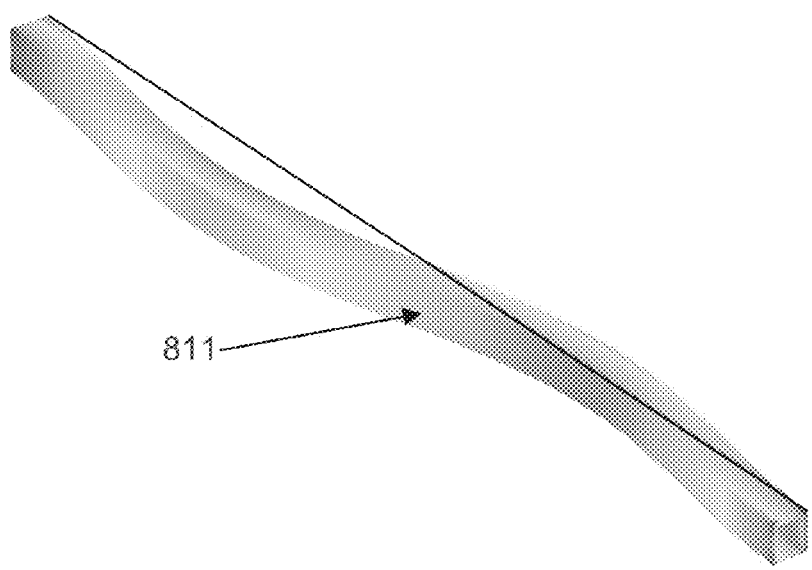

FIGS. 8A-8B show strain distribution for a single tube 811 with vibrational movements and Coriolis deflection movements, respectively. In some embodiments, sensing the tuning fork vibration and the Coriolis deflections can be achieved with a single transducer. For transducers near the center of the tube, the electrodes can be placed on either side of the tube and covering a center point of the tube. Electrodes located at the ends of the tube can sense both the tuning fork movements and Coriolis movements. In some implementations, multiphysics finite element analysis of the lateral sensor structure can be conducted to show that centrally located transducers yields a high performance when using a minimum number of electrodes for mass flow sensing.

As described with regards to FIG. 4D, separate coils can be used to actuate each tube portion, and sense the tuning fork vibration and Coriolis deflections of each tube to improve the zero bias performance. Similarly, both the centrally located and end located electrode arrangements shown in FIG. 6A and FIG. 6B can improve the zero bias performance of the dual-tube MEMS device.

Figure 7:
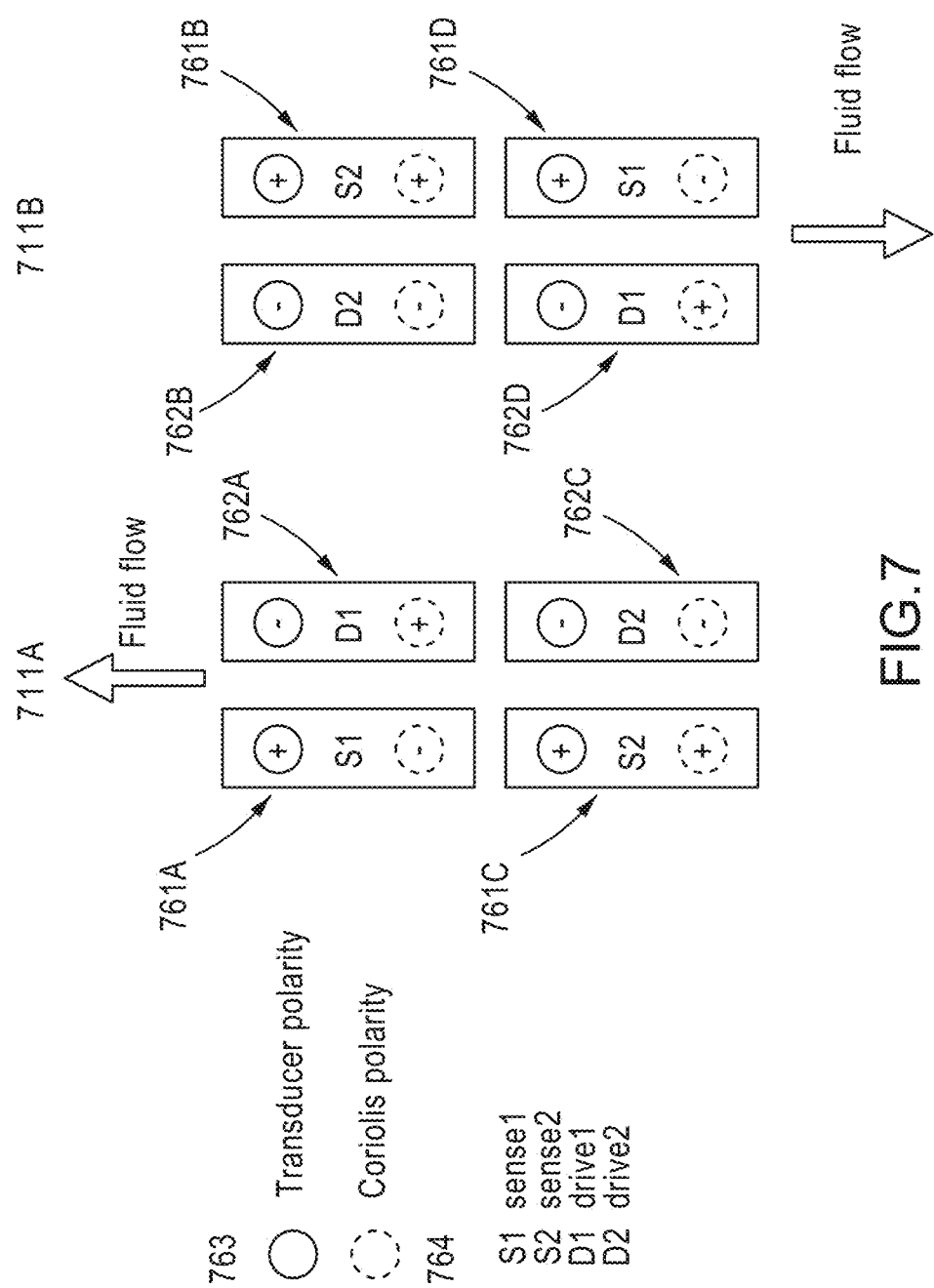
FIG. 7 shows a configuration of piezoelectric transducer placement in the dual-tube MEMS device, according to an embodiment.

FIG. 7 shows a configuration of piezoelectric transducer placement in a dual-tube MEMS device, according to an embodiment. In some embodiments, the material to be measured can flow through a first tube portion 711A of a micromachined tube in a direction opposite to the direction in which the material flows through a second tube portion 711B of the micromachined tube. In such arrangements, two actuator electrodes (762A and 762C) can be placed at the center of the first tube portion 711A, while two sensing electrodes (761A and 761C) can be also be placed at the center of the first tube portion 711A. Similarly, two actuator electrodes (762B and 762D) can be placed at the center of the second tube portion 711B, while two sensing electrodes (761B and 761D) can be also be placed at the center of the second tube portion 711B. As shown in FIG. 7, the circles with solid lines 763 indicate transducer polarity, and the circles with dotted lines 764 indicate polarity of Coriolis signals. In some implementations, the length of the electrodes is about 0.5-30% of the length of the tube so that both tuning fork mode and Coriolis flow can be measured with the same electrode. In some implementations, the electrodes can be grouped in pairs. In other implementations, the electrodes do not need to be grouped in pairs. In some implementations, the actuator electrodes 762A-762D can be used interchangeably with the sensing electrodes 761A-761D. Similarly stated, the actuator electrodes 762A-762D can be used to sense the tuning fork mode and Coriolis deflections, while the sensing electrodes 761A-761D can be used to actuate the vibrations of the micromachined tube. In some implementations, the Coriolis deflections are measured as a phase shift between the sensing electrodes S1 and S2. For example, the Coriolis deflections of the first tube portion 711A can be measured as a phase difference between the sensing electrodes 761A and 761C, and the Coriolis deflections of the second tube portion 711B can be measured as a phase difference between the sensing electrodes 761B and 761D.

Figure 9:
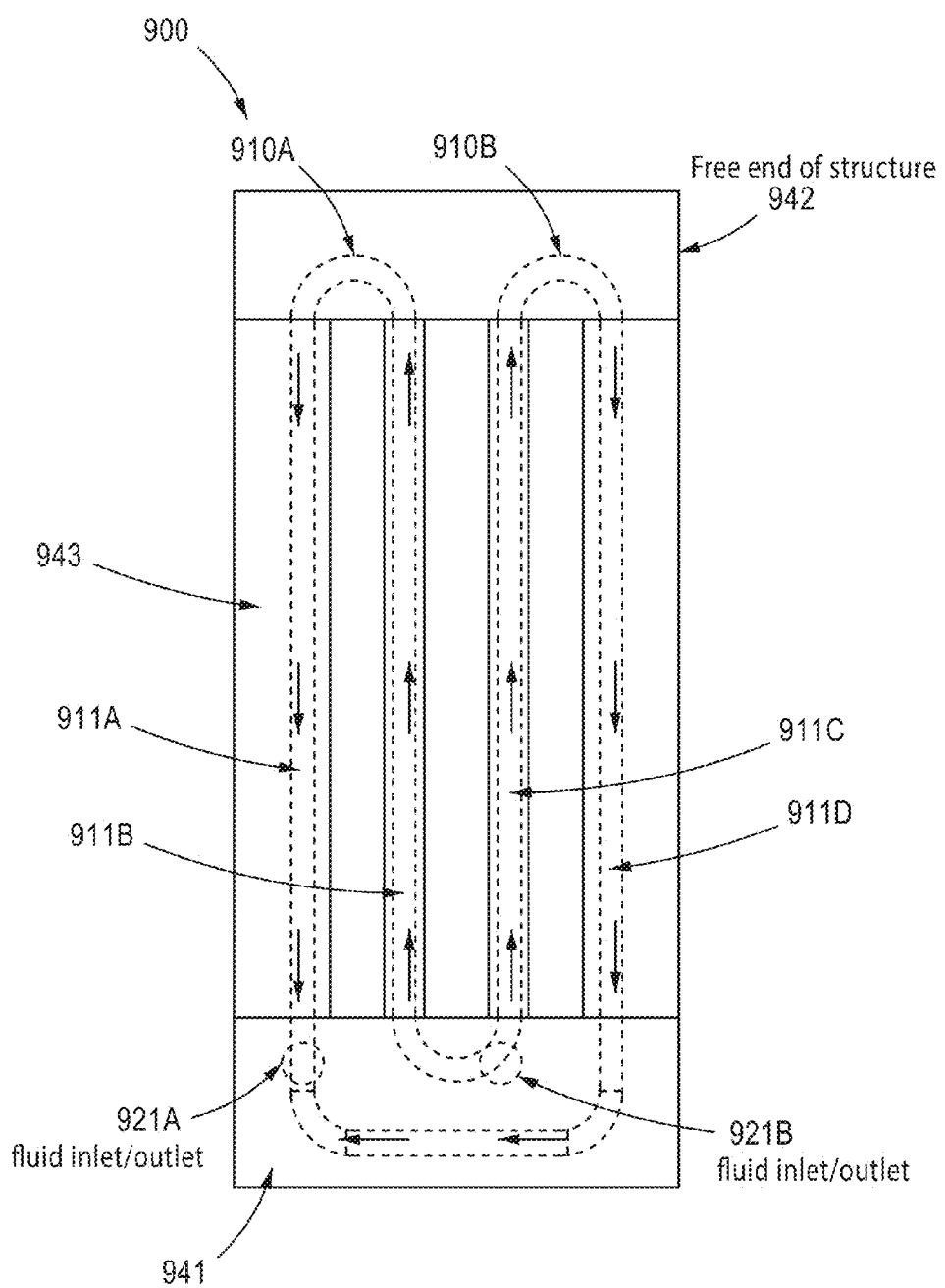
FIG. 9 shows a dual-tube MEMS device with parallel tube connections, according to an embodiment.

FIG. 9 shows a dual-tube MEMS device with parallel connections, according to an embodiment. In the implementation of the dual-tube MEMS device 400 shown in FIGS. 4A-4D the first tube portion and the second tube portion are in series in the flow path which provides about twice the pressure drop of a single tube. In some embodiments, the first tube portion and the second tube portion can be connected in parallel in the flow path, as shown in FIG. 9. The pressure drop in such a configuration is approximated half of pressure in defined single tube. In this configuration, the return path 911A and 911D for each tube 910A and 910B goes down along the frame 943 of the dual-tube MEMS device 900 and the two paths are connected in parallel at the bottom 941 of the sensor. Two apertures 921A and 921B can be in the flow path to allow inlet and outlet of the material. This allows one end 942 of the sensor structure to be free which eases packaging design and eliminates package-induced resonant frequency drift. With this flow path arrangement the pressure drop is less than the pressure drop in a single tube.

Figure 10:
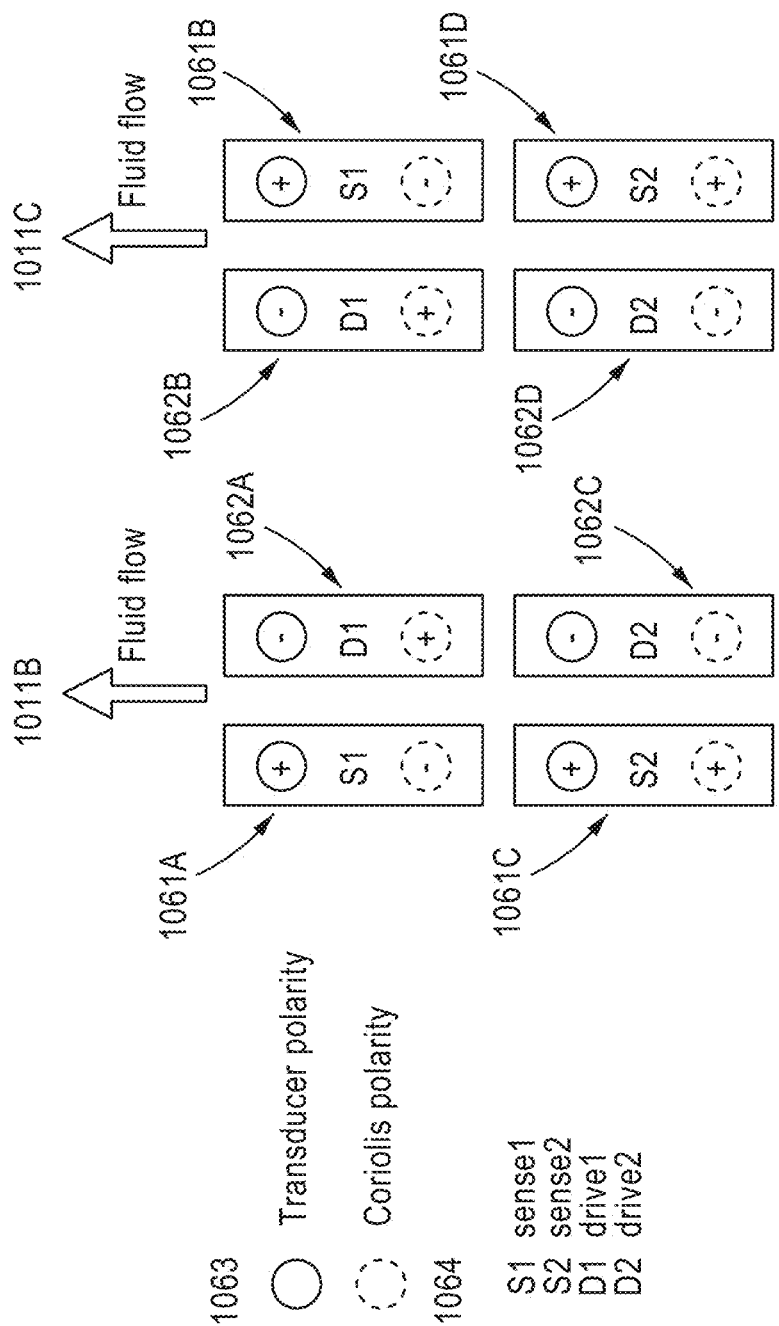
FIG. 10 shows a configuration of piezoelectric transducer placement in the dual-tube MEMS device with parallel tube connections, according to an embodiment.

FIG. 10 shows a configuration of piezoelectric transducer placement in a dual-tube MEMS device with parallel connections, according to an embodiment. In some embodiments, when the dual-tube MEMS device is fabricated with four tube portions connected in parallel, as described with regards to FIG. 9, the piezoelectric transducers can be placed in the center two tube portions such as 1011B and 1011C shown in FIG. 10. The material can flow through the two tube portions 1011B and 1011C in the same direction and return to the inlet/outlet portion (not shown in FIG. 10) through the other two tube portions (such as 911A and 911D shown in FIG. 9). In such arrangements, two actuator electrodes (1062A and 1062C) can be placed on the center of the first tube portion 1011B, while two sensing electrodes (1061A and 1061C) can also be placed on the center of the first tube portion 1011B. Similarly, two actuator electrodes (1062B and 1062D) can be placed on the center of the second tube portion 1011C, while two sensing electrodes (1061B and 1061D) can be also be placed on the center of the second tube portion 1011C. As shown in FIG. 10, the circles with solid lines 1063 indicate transducer polarity, and the circles with dotted lines 1064 indicate polarity of Coriolis signals. The electrodes can be placed on the center of the tube portions, on the ends of the tube portions, or on a combination of the center and ends of the tube portions, similar to the configurations discussed with regards to FIG. 7. In some implementations, as discussed with regards to FIG. 7, the Coriolis deflections are measured as a phase shift between the sensing electrodes S1 and S2. For example, the Coriolis deflections of the first tube portion 1011B can be measured as a phase difference between the sensing electrodes 1061A and 1061C, and the Coriolis deflections of the second tube portion 1011C can be measured as a phase difference between the sensing electrodes 1061B and 1061D.

FIG. 11 is a flow chart describing a method 1100 for operating the dual-tube MEMS device, according to an embodiment. In some embodiments, the method includes passing a material from an inlet portion of a tube to an outlet portion of the tube through an internal cavity passage, at 1102. The tube has a first tube portion and a second tube portion substantially parallel to the first tube portion. The first tube portion is coupled to the inlet portion and the second tube portion is coupled to the outlet portion. The internal cavity passage is defined at least in part by the first tube portion and the second tube portion.

The method further includes operating a drive element in contact with the tube to induce vibrational movements of the first tube portion and the second tube portion, at 1104. In some embodiments, the method includes sensing deflections of the first tube portion and the second tube portion, at 1106, and determining at least one property of the material based on the sensed deflections, at 1108.

While various embodiments have been described above, it should be understood that they have been presented by way of example only, and not limitation. Where methods and steps described above indicate certain events occurring in certain order, the ordering of certain steps may be modified. Additionally, certain of the steps may be performed concurrently in a parallel process when possible, as well as performed sequentially as described above. Although various embodiments have been described as having particular features and/or combinations of components, other embodiments are possible having any combination or sub-combination of any features and/or components from any of the embodiments described herein.

What is claimed is:

1. An apparatus, comprising:
    a base structure;
    a tube having a first tube portion, a second tube portion substantially parallel to the first tube portion, an inlet portion, and an outlet portion, the first tube portion being coupled to the inlet portion and the second tube portion being coupled to the outlet portion, the inlet portion and the outlet portion being connected to the base structure, the tube configured to have a material pass from the inlet portion to the outlet portion through a cavity defined at least in part by the first tube portion and the second tube portion;
    a first drive element in contact with the tube, the first drive element configured to carry a current;
    a second drive element configured to generate a magnetic field, the first drive element and the second drive element configured to vibrate the tube such that the first tube portion conducts vibrational movements substantially 180 degrees out of phase with vibrational movements of the second tube portion; and
    a plurality of sensing elements, at least a portion of a sensing element from the plurality of sensing elements being in contact with the tube, the plurality of sensing elements configured to sense deflections of the first tube portion and the second tube portion such that at least one property of the material is determined when the material passes through the tube and the tube is vibrated by the first drive element and the second drive element.

2. The apparatus of claim 1, wherein the first drive element includes a metal conductor, the metal conductor configured to be connected to an electricity generating source such that the current passes through the metal conductor.

3. The apparatus of claim 1, wherein the magnetic field is an asymmetric magnetic field, the sensing element from the plurality of sensing elements includes a metal conductor and the portion of the sensing element is a first portion of the sensing element,
    the sensing element includes a second portion of the sensing element, the second portion of the sensing element not in contact with the tube such that the deflections of the first tube portion and the second tube portion can be measured when the asymmetric magnetic field is applied to the first tube portion and the second tube portion.

4. The apparatus of claim 1, wherein the at least one property of the material includes at least one of mass flow rate, density, specific gravity, volumetric flow rate, dose, total volume delivered, temperature, chemical concentration, viscosity, or lubricity of the fluid.

5. The apparatus of claim 1, wherein the material includes at least one of a liquid, a gas, a slurry, a suspension containing a solid or liquid dispersed phase.

6. The apparatus of claim 1, wherein the sensing element from the plurality of sensing elements includes at least one piezoelectric electrode formed from a piezoelectric material, the at least one piezoelectric electrode being disposed on the first tube portion and covering a center point or an end point of the first tube portion.

7. The apparatus of claim 1, wherein the vibrational movements of the first tube portion and the vibrational movements of the second tube portion are in a first plane parallel to a second plane in which the first tube portion and the second tube portion lie.

8. The apparatus of claim 1, wherein the first drive element is in contact with the first tube portion and the current is a first current, the apparatus further comprising a third drive element in contact with the second tube portion, the third drive element configured to carry a second current, the first drive element, the second drive element, and the third drive element configured to vibrate the tube.

9. The apparatus of claim 1, wherein the magnetic field is asymmetric relative to a mid-point of the first tube portion.

10. The apparatus of claim 1, wherein the plurality of sensing elements is configured to sense the vibrational movements of the first tube portion and the vibrational movements of the second tube portion such that the first tube portion and the second tube portion are controlled to vibrate at a substantially constant amplitude.

11. A method, comprising:
    passing a material from an inlet portion of a tube to an outlet portion of the tube through an internal cavity passage, the tube having a first tube portion and a second tube portion substantially parallel to the first tube portion, the first tube portion being coupled to the inlet portion and the second tube portion being coupled to the outlet portion, the internal cavity passage being defined at least in part by the first tube portion and the second tube portion;
    operating a first drive element in contact with the tube and a second drive element not in contact with the tube to induce vibrational movements of the first tube portion and the second tube portion, the first drive element carrying a current, the second drive element generating a magnetic field, the vibrational movements of the first tube portion and the vibrational movements of the second tube portion being substantially 180 degrees out of phase;
    sensing deflections of the first tube portion and the second tube portion; and
    determining at least one property of the material based on the sensed deflections.

12. The method of claim 11, wherein the vibrational movements of the first tube portion and the second tube portion are substantially parallel to a plane defined by the tube.

13. The method of claim 11, wherein the first drive element includes a metal conductor.

14. The method of claim 11, wherein the magnetic field is an asymmetric field, and the sensing deflections of the first tube portion and the second tube portion includes:
    applying the asymmetric magnetic field to at least a portion of the tube; and
    receiving sensing signals through a first portion of a sensing element and a second portion of the sensing element, the first portion of the sensing element being in contact with the tube and the second portion of the sensing element being not in contact with the tube.

15. The method of claim 11, further comprising:
applying a cap structure on top of the tube, the cap structure being coupled to a frame structure of the tube via a resin sealant.

\* \* \* \* \*